(12) United States Patent
Asirvatham et al.

(10) Patent No.: US 12,239,536 B2
(45) Date of Patent: Mar. 4, 2025

(54) METHODS AND DEVICES FOR SECURING EPICARDIAL DEVICES

(71) Applicant: Mayo Foundation for Medical Education and Research, Rochester, MN (US)

(72) Inventors: Samuel J. Asirvatham, Rochester, MN (US); Paul A. Friedman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/367,980

(22) Filed: Sep. 13, 2023

(65) Prior Publication Data

US 2023/0414362 A1    Dec. 28, 2023

Related U.S. Application Data

(62) Division of application No. 16/647,062, filed as application No. PCT/US2018/050688 on Sep. 12, 2018, now Pat. No. 11,786,375.
(Continued)

(51) Int. Cl.
*A61N 1/05*        (2006.01)
*A61B 17/00*       (2006.01)
(Continued)

(52) U.S. Cl.
CPC ...... *A61F 2/2481* (2013.01); *A61B 17/32056* (2013.01); *A61N 1/0587* (2013.01);
(Continued)

(58) Field of Classification Search
CPC ........... A61F 2/2481; A61F 2002/2484; A61B 17/3468; A61N 1/0587; A61N 1/0597
See application file for complete search history.

(56) References Cited

U.S. PATENT DOCUMENTS

| 4,276,882 A | 7/1981 | Dickhudt et al. |
| 4,919,135 A | 4/1990 | Phillips, Jr. et al. |
| (Continued) |

FOREIGN PATENT DOCUMENTS

| WO | WO 2008/134755 A1 | 11/2008 | |
| WO | WO-2009081396 A2 * | 7/2009 | ......... A61B 17/0401 |

OTHER PUBLICATIONS

Extended European Search Report on European Appln. No. 18856581.6 dated Sep. 21, 2020, 6 pages.
(Continued)

*Primary Examiner* — Elizabeth Houston
*Assistant Examiner* — Lindsey Bachman
(74) *Attorney, Agent, or Firm* — Fish & Richardson P.C.

(57) ABSTRACT

This document describes methods and devices for securing epicardial devices. For example, this document describes methods and devices for securing epicardial devices by passing a sheath into a pericardial space of a patient through a first percutaneous access site, passing a guidewire through the sheath into the pericardial space of the patient, passing the guidewire through a transverse sinus of the patient, passing a snare device into the pericardial space through a second percutaneous access site, and capturing a free end portion of the guidewire using the snare device.

9 Claims, 4 Drawing Sheets

Related U.S. Application Data

(60) Provisional application No. 62/557,788, filed on Sep. 13, 2017.

(51) Int. Cl.
  *A61B 17/3205* (2006.01)
  *A61F 2/24* (2006.01)

(52) U.S. Cl.
  CPC ............... *A61B 2017/00358* (2013.01); *A61F 2002/2484* (2013.01)

(56) References Cited

U.S. PATENT DOCUMENTS

| | | | |
|---|---|---|---|
| 6,144,879 | A | 11/2000 | Gray |
| 6,612,978 | B2 | 9/2003 | Lau et al. |
| 7,389,134 | B1 | 6/2008 | Karicherla et al. |
| 7,981,020 | B2 | 7/2011 | Mortier et al. |
| 8,267,951 | B2 * | 9/2012 | Whayne ......... A61B 17/320016 606/190 |
| 11,219,772 | B2 | 1/2022 | Asirvatham et al. |
| 11,786,375 | B2 | 10/2023 | Asirvatham |
| 2004/0143154 | A1 | 7/2004 | Lau et al. |
| 2007/0005114 | A1 | 1/2007 | Salo et al. |
| 2007/0055091 | A1 | 3/2007 | Lau et al. |
| 2007/0203391 | A1 | 8/2007 | Bloom et al. |
| 2007/0233216 | A1 | 10/2007 | Liu et al. |
| 2008/0147157 | A1 | 6/2008 | Sweeney et al. |
| 2009/0177028 | A1 * | 7/2009 | White ................. A61M 60/438 600/37 |
| 2010/0004504 | A1 | 1/2010 | Callas et al. |
| 2010/0081867 | A1 | 4/2010 | Fishler et al. |
| 2013/0046356 | A1 | 2/2013 | Jensen et al. |
| 2013/0102849 | A1 * | 4/2013 | Criscione ............ A61M 60/289 600/204 |
| 2014/0018874 | A1 | 1/2014 | Zhu et al. |
| 2014/0107405 | A1 | 4/2014 | Hjelle et al. |
| 2015/0165104 | A1 | 6/2015 | Criscione et al. |
| 2016/0135973 | A1 | 5/2016 | Christakis et al. |
| 2016/0228699 | A1 | 8/2016 | Monteiro |
| 2017/0105675 | A1 | 4/2017 | Zhou et al. |
| 2020/0268513 | A1 | 8/2020 | Asirvatham |
| 2020/0330780 | A1 | 10/2020 | Asirvatham |

OTHER PUBLICATIONS

International Preliminary Report on Patentability in International Appln. No. PCT/US2018/050688 dated Mar. 17, 2020, 9 pages.
International Preliminary Report on Patentability in International Appln. No. PCT/US2018/057235 dated May 7, 2020, 7 pages.
International Search Report and Written Opinion in International Appln. No. PCT/US2018/050688 dated Jan. 4, 2019, 14 pages.
International Search Report and Written Opinion in International Appln. No. PCT/US2018/057235 dated Jan. 11, 2019, 13 pages.

* cited by examiner

METHODS AND DEVICES FOR SECURING EPICARDIAL DEVICES

CROSS-REFERENCE TO RELATED APPLICATIONS

This application is a divisional of U.S. application Ser. No. 16/647,062, filed Mar. 13, 2020, which is a National Stage application under 35 U.S.C. § 371 of International Application No. PCT/US2018/050688, having an International Filing Date of Sep. 12, 2018, which claims priority to U.S. Application Ser. No. 62/557,788, filed on Sep. 13, 2017. The disclosure of the prior application is considered part of the disclosure of this application, and is incorporated in its entirety into this application.

BACKGROUND

1. Technical Field

This document relates to methods and devices for securing epicardial devices. For example, this document relates to methods and devices for securing epicardial devices using the transverse sinus.

2. Background Information

The heart is surrounded by a pericardial sac, which is a conical sac of fibrous tissue. The pericardial sac includes an inner layer and an outer later and defines a space between the two layers, known as the pericardial cavity. The inner layer closely envelops the heart and is called the epicardium. The epicardium and heart define a space known as the epicardial space. Positioning of devices in the epicardial space can provide beneficial therapies such as stimulation, compression, pressure, and/or drug therapy.

SUMMARY

This document describes methods and devices for securing epicardial devices. For example, this document describes methods and devices for securing epicardial devices using the transverse sinus as a securement structure.

In one aspect, this disclosure is directed to a method of securing an implantable medical device on an epicardial surface. The method can include passing a sheath into a pericardial space of a patient through a first percutaneous access site, passing a guidewire through the sheath into the pericardial space of the patient, passing the guidewire through a transverse sinus of the patient, passing a snare device into the pericardial space through a second percutaneous access site, and capturing a free end portion of the guidewire using the snare device. In some cases, the first percutaneous access site can be a subxiphoid puncture. In some cases, the method can include passing the free end portion of the guidewire out the second percutaneous access site. In some cases, the method can include threading a device over the guidewire to be positioned near the epicardial surface. In some cases, the device can be a pacing electrode, a pacing electrode with insulation on one surface to prevent extracardiac stimulation, an ICD coil, a depot preparation of a drug, and/or a delivery system for biological therapies. In some cases, the sheath and the device can be a single unit that the guidewire is passed over. In some cases, the method can include slitting a portion of the sheath proximal the device and removing the portion of the sheath. In some cases, the sheath can be biodegradable. In some cases, the method can include passing a catheter through the sheath. In some cases, the method can include deflecting the catheter to pass the sheath into the pericardial space of the patient. In some cases, the method can include reducing a diameter of a distal portion of the sheath. In some cases, reducing the diameter of the distal portion of the sheath can maintain a tip portion of the catheter in the sheath. In some cases, the method can include securing the guidewire in place within the pericardial space.

In another aspect, this disclosure is directed to a method of securing an epicardial device. The method can include passing a sheath into a pericardial space of a patient using a first percutaneous access site, passing a guidewire comprising a first end and a second end from the sheath into the pericardial space of the patient, passing the guidewire through a transverse sinus of the patient, passing a snare device into the pericardial space using a second percutaneous access site, capturing a second end portion of the guidewire using the snare device, and securing the first end portion and the second end portion of the guidewire to a cap. In some cases, the first percutaneous access site can be a subxiphoid puncture. In some cases, the method can include threading an implantable medical device over the guidewire to be positioned near the heart. In some cases, the implantable medical device can be a pacing electrode, a pacing electrode with insulation on one surface to prevent extracardiac stimulation, an ICD coil, a depot preparation of a drug, and/or a delivery system for biological therapies. In some cases, the sheath and the implantable medical device can be a single unit that the guidewire is passed over. In some cases, the method can include slitting a portion of the sheath proximal the device and removing the portion of the sheath. In some cases, the sheath can be biodegradable. In some cases, the method can include passing a catheter through the sheath. In some cases, the method can include deflecting the catheter to pass the sheath into the pericardial space of the patient. In some cases, the method can include reducing a diameter of a distal portion of the sheath. In some cases, reducing the diameter of the distal portion of the sheath can maintain a tip portion of the catheter in the sheath. In some cases, the cap can be secured against an apex of the heart. In some cases, the guidewire can be tightened when securing the first end and the second end of the guidewire. In some cases, the method can include repeating the method to secure a plurality of guidewires to the cap.

In yet another aspect, this disclosure is directed to a method of securing an epicardial device. The method can include passing a sheath into a pericardial space of a patient using a first percutaneous access site, inflating a balloon on the sheath, passing a guidewire into the balloon using a second percutaneous access site, and capturing a free end of the guidewire using a snare device in the balloon. In some cases, the balloon can be expanded until the balloon substantially abuts a chest wall of the patient. In some cases, the method can include threading an implantable medical device over the guidewire to be positioned near the heart. In some cases, the implantable medical device can be a pacing electrode, a pacing electrode with insulation on one surface to prevent extracardiac stimulation, an ICD coil, a depot preparation of a drug, and/or a delivery system for biological therapies. In some cases, the sheath and the implantable medical device can be a single unit that the guidewire is passed over. In some cases, the method can include slitting a portion of the sheath proximal the device and removing the portion of the sheath. In some cases, the sheath is biodegradable. In some cases, the method can include passing a catheter through the sheath. In some cases, the method can include deflecting the catheter to pass the sheath into the pericardial space of the patient. In some cases, the method can include reducing a diameter of a distal portion of the sheath. In some cases, reducing the diameter of the distal portion of the sheath can maintain a tip portion of the catheter in the sheath. In some cases, the method can include reinflating the balloon after snaring. In some cases, the method can include advancing the sheath through the second percutaneous access site. In some cases, the balloon can be deflated while advancing the sheath through the second percutaneous access site. In some cases, the method can include securing the guidewire in place within the pericardial space.

In another aspect, this disclosure is directed to a system for securing an epicardial device. The system can include a plurality of wires, a cap configured for abutting an apex of a heart, where end portions of each of the plurality of wires are coupleable with the cap, and an implantable medical device that is engageable with one or more wires of the plurality of wires. In some cases, the implantable medical device can be securely positioned against an epicardium of the heart by the one or more wires of the plurality of wires and to deliver therapy to the heart. In some cases, the implantable medical device can be a pacing electrode, a pacing electrode with insulation on one surface to prevent extracardiac stimulation, an ICD coil, a depot preparation of a drug, and/or a delivery system for biological therapies. In some cases, the system can include a sheath that can pass over one or more of the plurality of wires. In some cases, the sheath can house the implantable medical device. In some cases, the sheath can be biodegradable. In some cases, the system can include a catheter that can pass through the sheath. In some cases, the catheter can be deflectable. In some cases, a diameter of a distal portion of the sheath can be modifiable. In some cases, reducing the diameter of the distal portion of the sheath can maintain a tip portion of the catheter in the sheath.

Particular embodiments of the subject matter described in this document can be implemented to realize one or more of the following advantages. Epicardial devices can be more effectively positioned in the pericardial space using the methods and devices described herein. Further, the devices positioned in the pericardial space can be more stable. In addition, the devices secured can limit injury to the heart and limit compromise to coronary circulation. The methods and devices provided herein can allow for extraction of defective and/or infected epicardial systems with less trauma as compared to some other methods and devices.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers represent corresponding parts throughout.

DETAILED DESCRIPTION

This document describes methods and devices for placing and securing epicardial devices, e.g., within the pericardial sac. For example, this document describes methods and devices for securing epicardial devices using the transverse sinus as a securement structure.

Positioning of devices in the epicardial space and/or the pericardial space can facilitate beneficial therapies such as cardiac rhythm stimulation, defibrillation, compression, pressure, reshaping, restraint, pumping, cooling, drug delivery therapy, just to provide a few examples. Epicardial devices can be more effectively positioned in the pericardial space using the methods and devices described herein as compared to conventional techniques that use anchor elements, self-restraining devices, and the like. Further, the devices positioned in the pericardial space can be more stable, limit injury to the heart, and limit compromise to the coronary circulation. The methods and devices provided herein can allow extraction of defective and/or infected epicardial systems.

Figure 1:
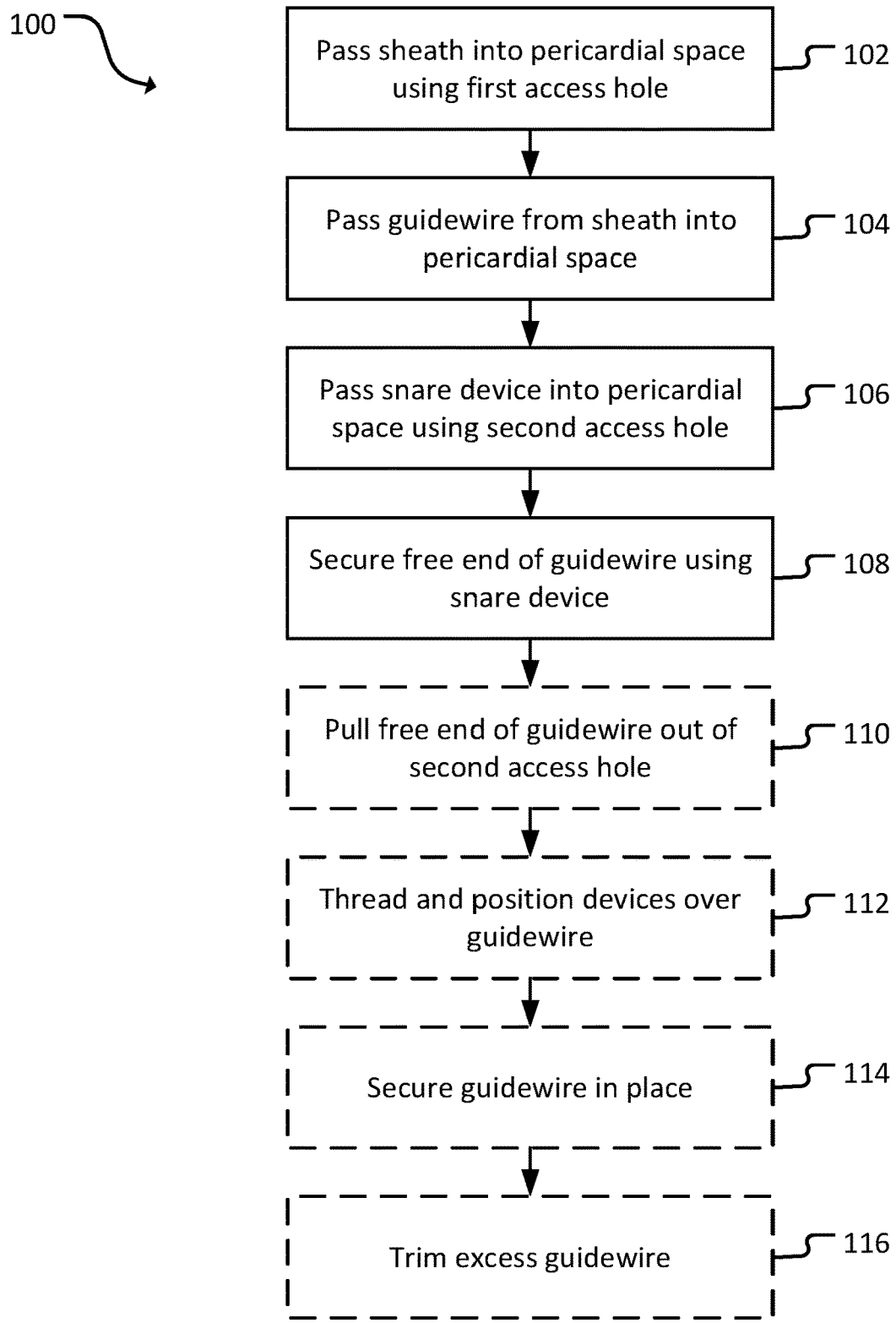
FIG. 1 is a flow chart of an example method of securing an epicardial device, in accordance with some embodiments provided herein.

Referring to FIG. 1, a method 100 of securing an epicardial device can include passing a sheath into a pericardial space of a patient through a first percutaneous site at operation 102, passing a guidewire through the sheath into the pericardial space of the patient at operation 104, passing a snare device into the pericardial space using a second percutaneous access site at operation 106, and capturing a free end portion of the guidewire using the snare device at operation 108.

Passing the sheath into the pericardial space of the patient through the first percutaneous access site at operation 102 can, in some cases, include passing the sheath into the pericardial space through a subxiphoid puncture for the first percutaneous access site. The sheath can be deflectable. In some cases, the sheath is a standard sheath. In some cases, the sheath can be used to facilitate transverse sinus securing of leads. For example, the sheath can be isodiametric, such that a distal segment of the sheath can have a diameter from about 1 mm to about 4 cm. In some cases, the diameter of the sheath can be reduced using a compression handle, a pull wire, or rotation of the sheath. Such a sheath can be passed over a guidewire until the sheath may not negotiate the curvature of the transverse sinus. In some cases, a deflectable catheter can then be passed through the sheath, while maintaining a tip of the catheter within the sheath. In some cases, the tip of the catheter can be maintained within the distal segment of the sheath by reducing the diameter of the distal segment of the sheath using the mechanisms described above. Accordingly, the sheath can be deflectable with the characteristics of the catheter and facilitate further maneuvering into an appropriate site.

Passing a guidewire from the sheath into the pericardial space of the patient at operation 104 can include navigating the guidewire into the transverse sinus of the patient. In some cases, navigating the guidewire can include advancing the guidewire from left to right. In some cases, navigating the guidewire from the sheath into the transverse sinus of the patient at operation 104 can include advancing the guidewire from right to left. In some cases, the guidewire can be passed just behind and above the left atrial appendage of the patient. In some cases, the guidewire can be deflectable (steerable). In some cases, a catheter can be used instead of the guidewire. In some cases, the catheter can be deflectable (steerable).

Passing a snare device into the pericardial space using a second percutaneous access site at operation 106 can include passing the snare to the right portion of the transverse sinus, e.g., near the superior vena cava. In some cases, the snare is a lasso device.

Securing a free end portion of the guidewire using the snare device at operation 108 can include capturing or snaring the free end portion of the guidewire and pulling the guidewire further through the transverse sinus. In some cases, securing a free end portion of the guidewire 108 can include threading two portions of the guidewire into a single sheath (with the portion of the guidewire within the transverse sinus in between the two portions of the guidewire).

In some cases, the method 100 of securing an epicardial device can include pulling the free end portion of the guidewire out of the second percutaneous access site at operation 110.

In some cases, the method 100 of securing an epicardial device can include threading and positioning devices over the guidewire at operation 112. In some cases, the devices can include one or more pacing electrodes, pacing electrodes with insulation on one surface to prevent extracardiac stimulation, ICD coils, depot preparations of various drugs for slow absorption into the pericardium and systemic vasculature, delivery systems for biological therapies such as stem cell reservoirs, skeletal myoblasts, or other regeneration-provoking agents that require prolonged and stable contact. In some cases, the guidewire can be insulated with denuded areas that form electrodes. In some cases, operation 112 can include placing defibrillator coils. In some cases, the defibrillator coils can be specifically designed for this access. For example, the defibrillator coils can be delivered over the wire and include short, self-insulated segments that provide bipolar coils in series. In some cases, the coils can be used coupled together to act as an anode or cathode for defibrillation. Such a configuration can allow for selective defibrillation of the atria, ventricles, or both. In some cases, when the coils are not connected in series, the coils can be used as pacing electrodes.

In some cases, the sheath and electrodes (e.g., pacing electrodes and/or defibrillation coils) can be a single unit, such that the entire unit is threaded over the guidewire at 104. In some cases, after access is gained to the transverse sinus, and the sheath and electrodes are passed over the guidewire, a slitter can be used proximal the electrodes such that a proximal portion of the sheath can be removed. In some cases, the guidewire can be removed. In some cases, the sheath can be biodegradable, such that the sheath can be left in place until adequate position can be confirmed (e.g., over a period of days or weeks), and then the sheath can be left to degrade.

In some cases, the method 100 of securing an epicardial device can include securing the guidewire in place at operation 114. In some cases, securing the guidewire can include placing a suture lock, or other locking mechanism, over both end portions of the guidewire. In some cases, securing the guidewire can include placing a suture lock, or other locking mechanism, over each end portion of the guidewire. In some cases, the guidewire is secured inside the pericardial sac. In some cases, the guidewire is secured outside the pericardial sac. In some cases, the guidewire is secured at the apex of the heart. In some cases, the guidewire is secured at another location of the heart. In some cases, securing the guidewire includes tightening the guidewire to apply a pressure to the heart. In some cases, the method 100 of securing an epicardial device can include trimming excess guidewire material at operation 116.

In some cases, guidewires can be navigated through the transverse sinus from the left and create a loop.

In some cases, one or more guidewires can be navigated to enter the transverse sinus from the right side, and can be navigated to exit the left side of the transverse sinus. Then, a sheath (e.g., a deflectable sheath) can be passed into the transverse sinus over the guidewire. A snare (e.g., a deflectable snare), or any catching device, can then be passed through the sheath and positioned to surround and capture the left atrial appendage (LAA). In some cases, the sheath can then be moved distally or proximally in relation to the LAA in order to loosen or tighten tension of the snare around the LAA. In some cases, a locking mechanism can be passed to the snare to lock the snare around the left atrial appendage for long term placement (e.g., to close the LAA in effort to prevent embolic strokes). In some cases, the locking mechanism can be passed from inside the sheath. In some cases, the locking mechanism can be passed over the sheath.

In some cases, the guidewire can pass through the transverse sinus twice, once anteriorly and once posteriorly to the appendage. The guidewires can then be secured to occlude the left atrial appendage without damaging the underlying vasculature, including the left main and proximal coronary arteries.

In some cases, the guidewire can pass posteriorly to the appendage to advance an expanded component to compress and occlude the left atrial appendage near the ostium.

In some cases, the guidewire can be passed around the left ventricular inlet and atrioventricular grooves to produce mild compression as a treatment for annular dilation and atrioventricular valve regurgitation.

Figure 2:
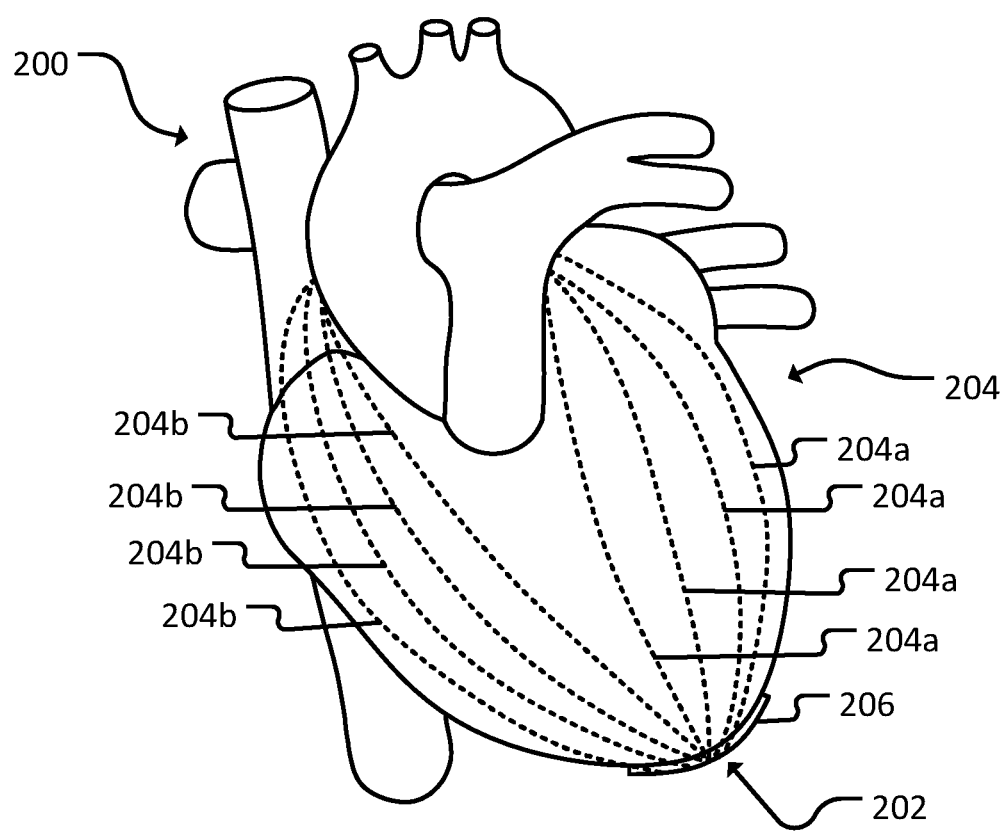
FIG. 2 is a schematic of a multi-wire scaffolding system on a heart, in accordance with some embodiments provided herein.

Referring to FIG. 2, a multi-wire scaffolding system 202 on a heart 200 can include a plurality of guidewires 204 (shown in dashed lines to enhance visibility of guidewires 204) and a cap 206.

In some cases, guidewires 204 surround the heart longitudinally. While FIG. 2 only shows guidewires 204 positioned longitudinally along the anterior side of heart 200, it should be understood that guidewires 204 may also be similarly positioned longitudinally along the posterior side of heart 200. Plurality of guidewires 204 can include first end portions 204*a* and second end portions 204*b*. In some cases, one or more of the plurality of guidewires 204 can be fed through the transverse sinus. In some cases, the transverse sinus can provide a first stabilizing site for guidewires 204. In some cases, both first end portions 204*a* and second end portions 204*b* of guidewires 204 can be secured to or around cap 206. In some cases, additional guidewires can surround the heart transversely. In some cases, guidewires 204 can apply varying amounts of pressure to heart 200 to mechanically compress or restrain heart 200. In some cases, guidewires 204 can be along an obtuse margin of heart 200. In some cases, guidewires 204 can be along an acute margin of heart 200. In some cases, as described above, guidewires 204 can be used to secure one or more devices to heart 200. Such devices can facilitate beneficial therapies such as cardiac rhythm stimulation, pacing, compression, pressure, reshaping (e.g., reshaping of a mitral valve to treat regurgitation), restraint against dilation (e.g., to treat heart failure), pumping assistance, cooling, drug delivery therapy, and the like.

In some cases, cap 206 can provide a second stabilizing site for the plurality of guidewires 204. In some cases, cap 206 can abut the apex of heart 200. In some cases, cap 206 can minimize slippage of the second stabilizing site. In some cases, cap 206 can protect heart 200 from first end portions 204a and second end portions 204b of the plurality of guidewires 204. In some cases, cap 206 can be located in the pericardial sac. In some cases, cap 206 can be located outside the pericardial sac. In some cases, cap 206 can be located near the apex of heart 200. In some cases, cap 206 is approximately 2 mm by approximately 4 mm. In some cases, cap 206 can be malleable. In some cases, cap 206 can be foldable. In some cases, cap 206 can be made of plastic. In some case, cap 206 can be made of nitinol. In some cases, cap 206 has a curvature. In some cases, cap 206 is concave facing the apex of heart 200. In some cases, cap 206 can include holes to receive first end portions 204a and second end portions 204b of plurality of guidewires 204. In some cases, each of first end portions 204a and second end portions 204b can be received by separate holes in cap 206. In some cases, multiple of first end portions 204a and second ends end portions 204b can be received by a single hole in cap 206. In some cases, cap 206 can include slots to receive first end portions 204a and second end portions 204b. In some cases, cap 206 can include notches to receive first end portions 204a and second end portions 204b. In some cases, first end portions 204a can be tied to second end portions 204b to secure plurality of guidewires 204 to cap 206. In some cases, knots can be tied individually on first end portions 204a and second end portions 204b to secure plurality of guidewires 204 on cap 206. In some cases, suture locks can be placed on first end portions 204a and second end portions 204b to secure plurality of wire 204 to cap 206.

Figure 3:
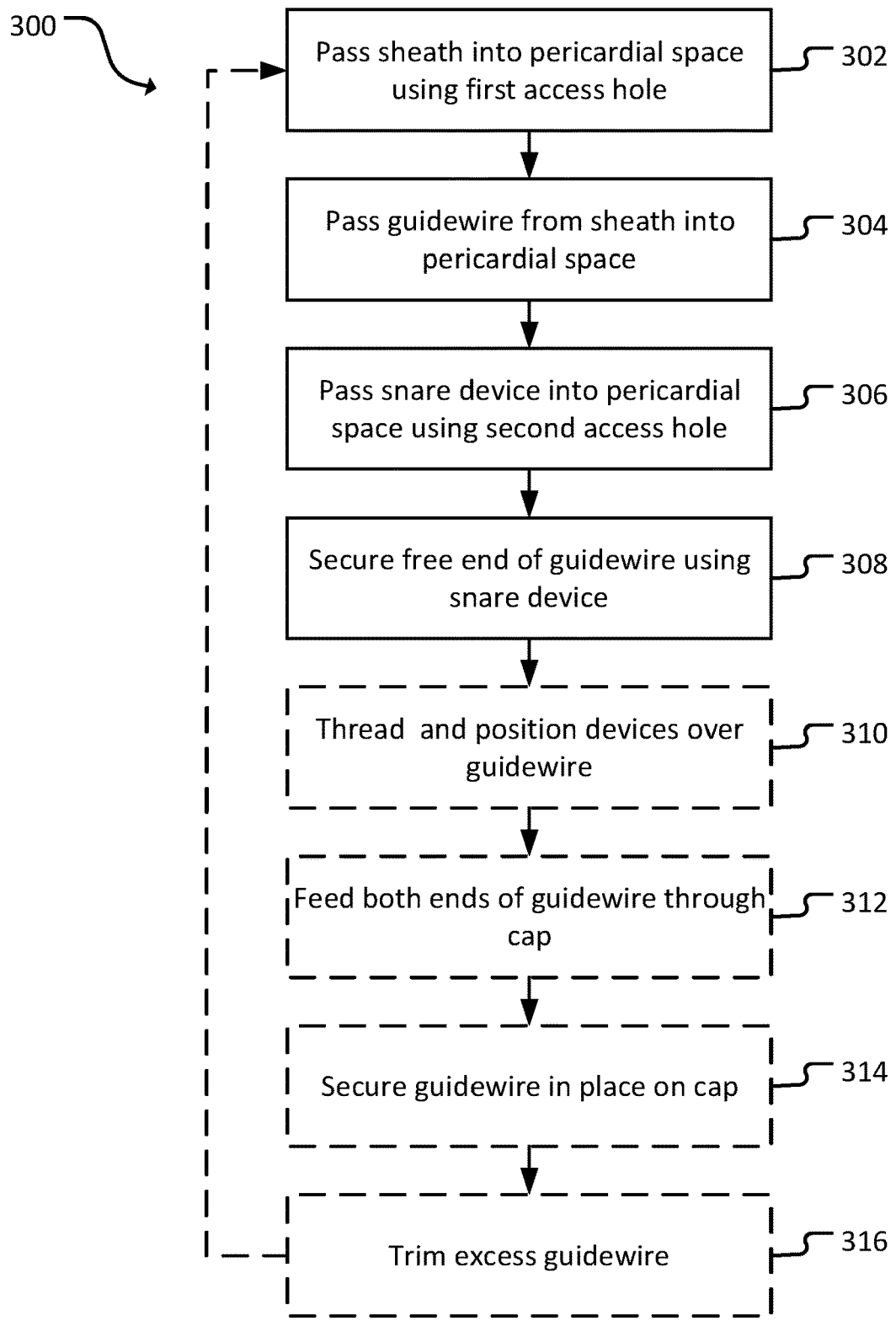
FIG. 3 is a flow chart of a second example method of securing an epicardial device, in accordance with some embodiments provided herein.

Referring to FIG. 3, another example method 300 of securing an epicardial device can include passing a sheath into a pericardial space of a patient using a first percutaneous access site at operation 302, passing a guidewire through the sheath into the pericardial space of the patient at operation 304, passing a snare device into the pericardial space using a second percutaneous access site at operation 306, and capturing a free end portion of the guidewire using the snare device at operation 308. Operations 302-308 can be substantially similar to operations 102-108 of method 100. In some cases, method 300 can include threading and positioning devices over the guidewire at operation 310. Operation 310 can be substantially similar to operation 112 of method 100.

In some cases, the method 300 of securing an epicardial device can include feeding both free end portions of the guidewire through or onto a cap at operation 312. In some cases, the cap can be cap 206, as described with reference to FIG. 2.

In some cases, the method 300 of securing an epicardial device can include securing the guidewire on the cap in place at operation 314.

In some cases, securing the guidewire can include placing a suture lock, or other locking mechanism, over both end portions of the guidewire once the guidewire is through the cap. In some cases, securing the guidewire can include placing a suture lock, or other locking mechanism, over each end portion of the guidewire once the guidewire is through the cap. In some cases, the guidewire is secured inside the pericardial sac on the cap. In some cases, the guidewire is secured outside the pericardial sac on the cap. In some cases, the guidewire is secured at the apex of the heart on the cap. In some cases, the guidewire is secured at another location of the heart on the cap. In some cases, securing the guidewire includes tightening the guidewire to apply a pressure or compression to the heart. In some cases, securing the guidewire can include buffers (e.g., pads, balloons, bladders, etc.), such that when the guidewires are tightened and secured, the buffers increase the pressure at selected locations of the heart. In some cases, the buffers can cause the heart to be locally reshaped. In some cases, the method 300 of securing an epicardial device can include trimming excess guidewire material at 316.

In some cases, method 300 can be repeated, such that multiple guidewires are secured around various locations of the heart, such as described with respect to FIG. 2. In some cases, method 300 can allow devices to be placed in any location around the heart. In some cases, method 300 can allow tightening of guidewires after initial implantation via the cap.

Figure 4:
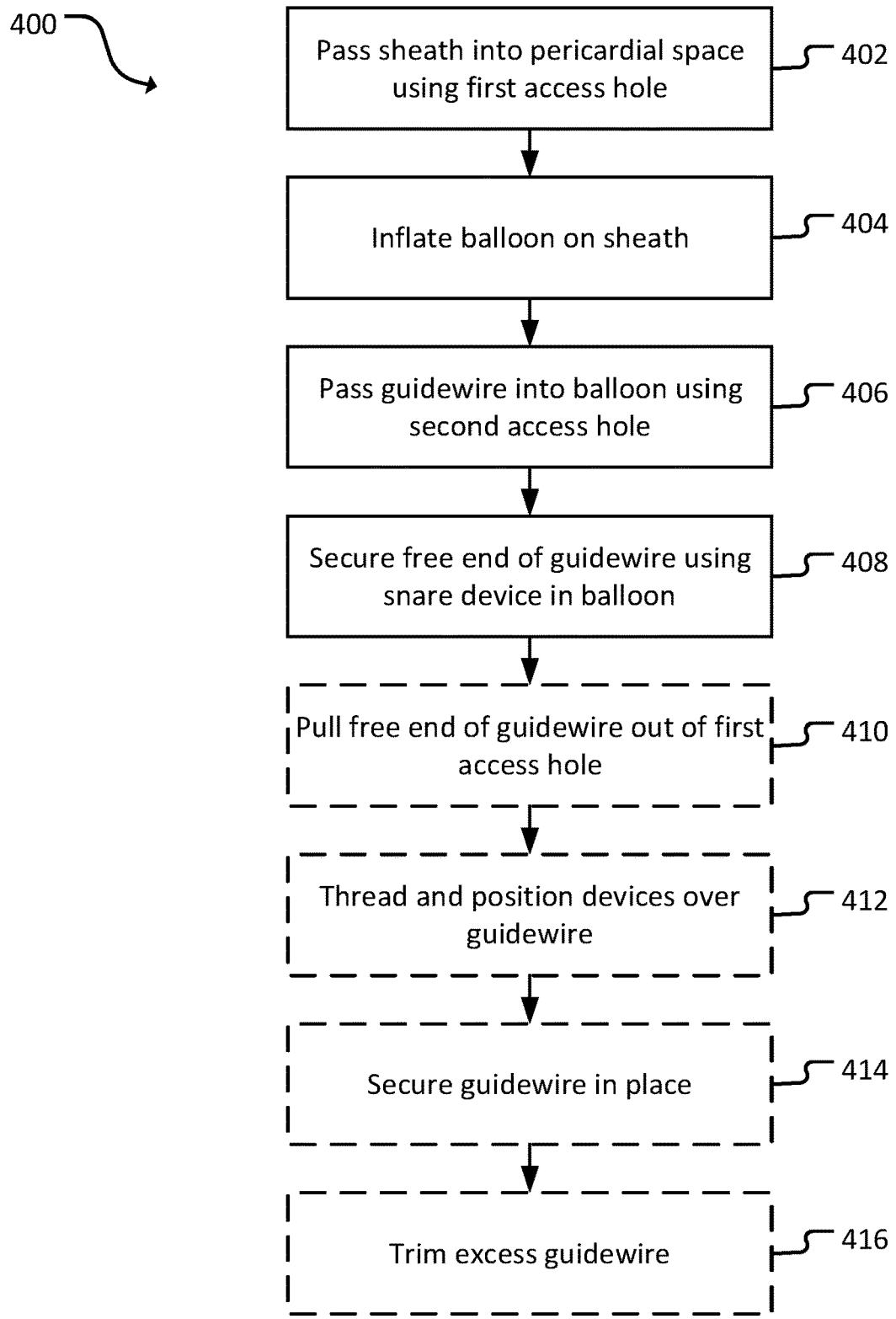
FIG. 4 is a flow chart of a third example method of securing an epicardial device, in accordance with some embodiments provided herein.

Referring to FIG. 4, a method 400 of securing an epicardial device can include passing a sheath into a pericardial space of a patient using a first percutaneous access site at operation 402, inflating a balloon on the sheath at operation 404, passing a guidewire into the balloon using a second percutaneous access site at operation 406, and capturing a free end portion of the guidewire using a snare device in the balloon at operation 408.

Passing the sheath into the pericardial space of the patient using the first percutaneous access site at operation 402 can include passing the sheath into the pericardial space using a subxiphoid puncture for the first percutaneous access site. The sheath can be deflectable (steerable). The sheath can include a balloon located at a distal end portion of the sheath. In some cases, the sheath is a standard sheath. In some cases, the sheath can be used to facilitate transverse sinus securing of leads. For example, the sheath can be isodiametric, such that a distal segment of the sheath can have a diameter from about 1 mm to about 4 cm. In some cases, the diameter of the sheath can be reduced using a compression handle, a pull wire, or rotation of the sheath. Such a sheath can be passed over a guidewire until the sheath may not negotiate the curvature of the transverse sinus. In some cases, a deflectable catheter can then be passed through the sheath, while maintaining a tip of the catheter within the sheath. In some cases, the tip of the catheter can be maintained within the distal segment of the sheath by reducing the diameter of the distal segment of the sheath using the mechanisms described above. Accordingly, the sheath can be deflectable with the characteristics of the catheter and facilitate further maneuvering into an appropriate site.

Inflating the balloon on the sheath at operation 404 can include inflating the balloon with a fluid (e.g., saline, air, or gel). In some cases, inflating the balloon at operation 404 can include inflating the balloon inside the pericardial sac. In some cases, the balloon can be inflated until the balloon abuts the chest wall. When the balloon is expanded until the balloon abuts the chest wall, anatomy (e.g., lungs) can be moved out of the way providing direct access to the pericardial sac without interacting with other anatomy. In some cases, the balloon can be expanded on the lateral left cardiac surface near the apex of the heart. In some cases, the balloon can be filled with a radiopaque or ultra-sound detected material so that radiography or ultrasound can be used to determine when the balloon has been expanded to a desired location (e.g., the chest wall). In some cases, the inflated balloon can provide safe access for a second puncture at a plurality of otherwise undesirable locations. For example, the inflated balloon can facilitate a second pericardial access location. In some cases, the balloon can be configured to inflate more substantially on one side than the other such that the heart does not experience extensive pressure when the balloon is inflated. For example, the balloon can have multiple chambers with one chamber being larger than the other. In some cases, the balloon can have a flat side that abuts the heart. In some cases, the balloon can be shaped as a half ellipsoid, half sphere, or a half cylinder. In some cases, the balloon can expand between approximately 5 mm and approximately 6 cm. In some cases, one side of the balloon is made of a material that is more compliant than a material on the opposite side of the balloon. Such a balloon (with differentially-compliant walls) can facilitate unilateral expansion when pressurized. In some cases, once the second pericardial access is obtained, a stiff but deflectable lasso can be used to snare proximal to the balloon. In some cases, the balloon can be reinflated after snaring. In some cases, the balloon is gradually deflated as the delivery sheath or an initial deployment tool is advanced out through the second puncture, facilitating two different punctures to stabilize both ends of the bead, coils, or delivery tool, which can be secured using methods described herein, such as a hub cap, or apical stabilizer.

Passing a guidewire into the balloon using a second percutaneous access site at operation 406 can include passing the guidewire into the transverse sinus of the patient. In some cases, passing the guidewire can include advancing the guidewire from left to right. In some cases, passing a guidewire from the sheath into a transverse sinus of the patient at operation 406 can include advancing the guidewire from right to left. In some cases, the guidewire can be passed just behind and above the left atrial appendage of the patient. In some cases, the guidewire can be deflectable. In some cases, the guidewire can be a catheter. In some cases, the catheter can be deflectable.

In some cases, the sheath and electrodes (e.g., pacing electrodes and/or defibrillation coils) can be a single unit, such that the entire unit is threaded over the guidewire at 406. In some cases, after access is gained to the transverse sinus, and the sheath and electrodes are passed over the guidewire, a slitter can be used proximal the electrodes such that a proximal portion of the sheath can be removed. In some cases, the guidewire can be removed. In some cases, the sheath can be biodegradable, such that the sheath can be left in place until adequate position can be confirmed (e.g., over a period of days or weeks), and then the sheath can be left to degrade.

Capturing a free end portion of the guidewire using a snare device in the balloon at operation 408 can include passing the snare device into a lumen of the balloon. In some cases, the snare device can be in a location such that when the free end portion of the wire is passed through the balloon, the free end portion of the guidewire is also passed through the snare device. In some cases, the snare device can capture the free end portion of the guidewire and pass the guidewire through the transverse sinus. In some cases, the snare device is a lasso device.

In some cases, the method 400 of securing an epicardial device can include pulling the free end portion of the wire out of the first percutaneous access site at operation 410. In some cases, the free end portion of the guidewire can be pulled through a third percutaneous access site such that multiple percutaneous epicardial accesses.

In some cases, the method 400 of securing an epicardial device can include threading and positioning devices over the guidewire at operation 412. In some cases, the devices can include one or more pacing electrodes, pacing electrodes with insulation on one surface to prevent extracardiac stimulation, ICD coils, depot preparations of various drugs for slow absorption into the pericardium and systemic vasculature, delivery systems for biological therapies such as stem cell reservoirs, skeletal myoblasts, or other regeneration-provoking agents that require prolonged and stable contact. In some cases, the guidewire can be insulated with denuded areas that form electrodes. In some cases, operation 412 can include placing defibrillator coils. In some cases, the defibrillator coils can be specifically designed for this access. For example, the defibrillator coils can be delivered over the wire and include short, self-insulated segments that provide bipolar coils in series. In some cases, the coils can be used coupled together to act as an anode or cathode for defibrillation. Such a configuration can allow for selective defibrillation of the atria, ventricles, or both. In some cases, when the coils are not connected in series, the coils can be used as pacing electrodes.

In some cases, the method 400 of securing an epicardial device can include securing the guidewire in place at operation 414. In some cases, securing the guidewire can include placing a suture lock, or other locking mechanism, over both end portions of the guidewire. In some cases, securing the guidewire can include placing a suture lock, or other locking mechanism, over each end portion of the guidewire. In some cases, the guidewire is secured inside the pericardial sac. In some cases, the guidewire is secured outside the pericardial sac. In some cases, the guidewire is secured at the apex of the heart. In some cases, the guidewire is secured at another location of the heart. In some cases, securing the guidewire includes tightening the guidewire to apply a pressure to the heart. In some cases, the guidewire is secured using a cap, similar to as described in operation 314 of method 300. In some cases, the method 400 of securing an epicardial device can include trimming excess guidewire material at operation 416.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures does not necessarily require the particular order shown, or sequential order, to achieve desirable results. In certain implementations, multitasking and parallel processing may be advantageous.

What is claimed is:

1. A method of securing an implantable medical device on an epicardial surface, the method comprising:
   passing a sheath into a pericardial space of a patient through a first percutaneous access site;
   passing a guidewire comprising a first end and a second end through the sheath into the pericardial space of the patient;
   passing the guidewire through a transverse sinus of the patient;
   passing a snare device into the pericardial space through a second percutaneous access site;
   capturing a free end portion of the guidewire using the snare device;
   threading the implantable medical device over the guidewire to be positioned near the epicardial surface; and
   securing the first end and the second end of the guidewire to a hole, a slot, or a notch defined by a cap configured to abut an apex of a heart of the patient such that the guidewire forms a loop that begins and ends at the cap,
   wherein the guidewire comprises one or more denuded portions that are configured to function as one or more electrodes, and
   wherein the implantable medical device comprises a defibrillator coil.

2. The method of claim 1, further comprising passing the free end portion of the guidewire out the second percutaneous access site.

3. The method of claim 1, wherein the implantable medical device is at least one of a pacing electrode, a pacing electrode with insulation on one surface to prevent extracardiac stimulation, an ICD coil, a depot preparation of a drug, and a delivery system for biological therapies.

4. The method of claim 1, further comprising passing a catheter through the sheath and deflecting the catheter to pass through the sheath into the pericardial space of the patient.

5. The method of claim 4, further comprising reducing a diameter of a distal portion of the sheath, wherein reducing the diameter of the distal portion of the sheath maintains a tip portion of the catheter in the sheath.

6. The method of claim 1, further comprising securing the guidewire in place within the pericardial space.

7. The method of claim 1, wherein the first percutaneous access site is a subxiphoid puncture, and wherein the sheath and the device are a single unit such that the single unit is threaded over the guidewire.

8. The method of claim 1, further comprising slitting a portion of the sheath proximal the device and removing the portion of the sheath, wherein the sheath is biodegradable.

9. The method of claim 1, wherein the guidewire is configured to apply an amount of pressure to the heart to mechanically compress or restrain the heart.

* * * * *